United States Patent [19]

Gallo et al.

[11] 4,064,237

[45] Dec. 20, 1977

[54] SYNERGISTIC PESTICIDAL MIXTURES OF PHOSALONE AND MALATHION AND PROCESS FOR CONTROLLING ARTHROPODS THEREWITH

[75] Inventors: Michael A. Gallo, Belle Meade, N.J.; Der-I Wang, Taipei, China /Taiwan

[73] Assignee: Rhodia, Inc., New York, N.Y.

[21] Appl. No.: 647,262

[22] Filed: Jan. 5, 1976

Related U.S. Application Data

[63] Continuation-in-part of Ser. No. 550,902, Feb. 18, 1975, abandoned.

[51] Int. Cl.$^2$ .............................................. A01N 9/36
[52] U.S. Cl. .................................... 424/200; 424/212; 424/213
[58] Field of Search ..................... 424/200, 212, 213

[56] References Cited

FOREIGN PATENT DOCUMENTS 1,005,372  9/1965  United Kingdom.
 789,358  1/1958  United Kingdom.

*Primary Examiner*—V. D. Turner

[57] ABSTRACT

Synergistic pesticidal mixtures are provided that are effective against arthropods such as insects and mites, comprising an O,O-dialkyl diphosphoryl methyl halo-6-benzoxazolone, such as phosalone, and an O,O-dialkyl-(1,2-dicarbalkoxylalkyl)diphosphate, such as malathion.

A process is also provided for control of arthropods, i.e., insects and mites, using a mixture of these two compounds.

7 Claims, No Drawings

SYNERGISTIC PESTICIDAL MIXTURES OF PHOSALONE AND MALATHION AND PROCESS FOR CONTROLLING ARTHROPODS THEREWITH

This application is a continuation-in-part of Ser. No. 550,902 filed Feb. 18, 1975, and now abandoned.

O,O-dialkyl dithiophosphoryl methyl halo-6-benzoxazolones have been proposed as insecticides and miticides or acaricides in French Pat. No. 1,277,401 and British Pat. No. 1,005,372 to Rhone-Poulenc. Certain of these compounds also are indicated as possessing parasiticidal properties, in British Pat. No. 1,164,028 and French Pat. No. 1,482,025 to Rhone-Poulenc. It has not however been suggested that mixtures of these compounds with other phosphate esters be employed or have advantageous properties.

Phosphate esters such as S-(1,2-dicarbalkoxyalkyl-)O,O-dialkyl dithiophosphates have also been known as insecticidal. Such compounds were developed in Germany during World War II, and became available following the war upon release of previously secret German technology in this field. However, these have not been proposed for combination with other phosphate esters.

In accordance with the invention, it has been determined that a mixture of these two types of phosphate esters is synergistically more effective than either ester taken alone, and that the mixture is particularly effective against arthropods, such as insects and mites. These two types of compounds are sufficiently similar in structure, since both have a phosphate or thiophosphate nucleus with two homologous alkoxy substituents attached thereto, that it is surprising that one has a synergistic or activity-enhancing effect on the other, when used in combination.

The O,O-dialkyl diphosphoryl methyl halo-6-benzoxazolones employed in the synergistic mixtures of the invention have the structure:

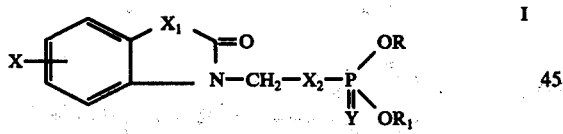

wherein X represents a hydrogen or halogen atom, such as fluorine, chlorine, bromine, or iodine; R and $R_1$ represent alkyl groups containing from one to about four carbon atoms, $X_1$ and $X_2$ represent an oxygen or sulphur atom, and Y represents an oxygen or sulphur atom. $X_1$ and $X_2$ and Y can be the same or different.

Preferably, $X_1$ is oxygen, $X_2$ is sulphur and R and $R_1$ are ethyl, in which case the compound is phosalone, O,O-diethyl dithiophosphoryl methyl-3-chloro-6-benzoxazolone. This compound has the structure:

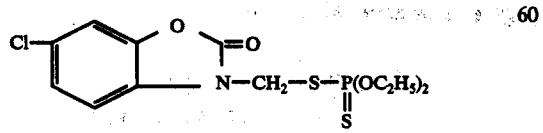

Also useful is O,O-diethyl-dithiophosphoryl methyl-3-benzothiazolone.

Additional compounds which can be used include:

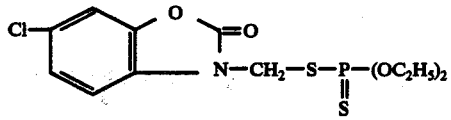

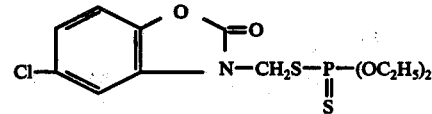

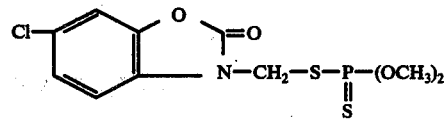

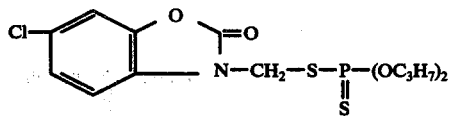

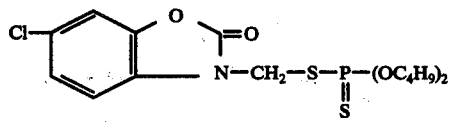

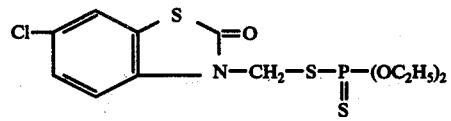

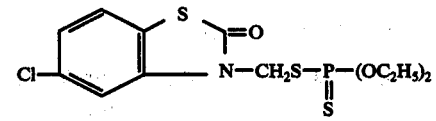

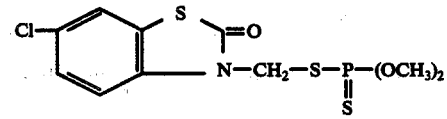

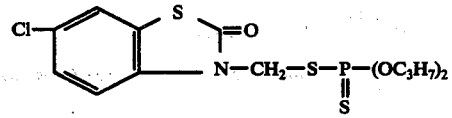

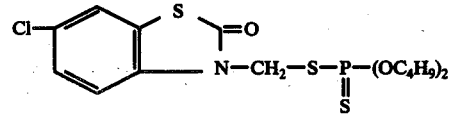

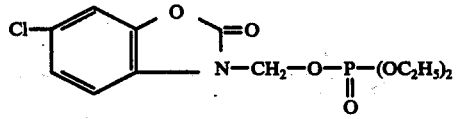

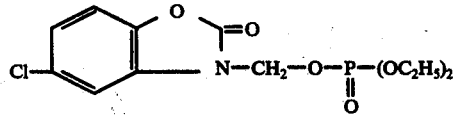

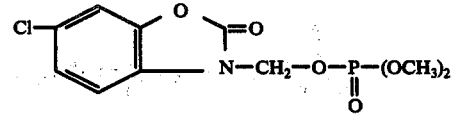

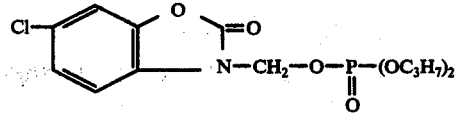

-continued
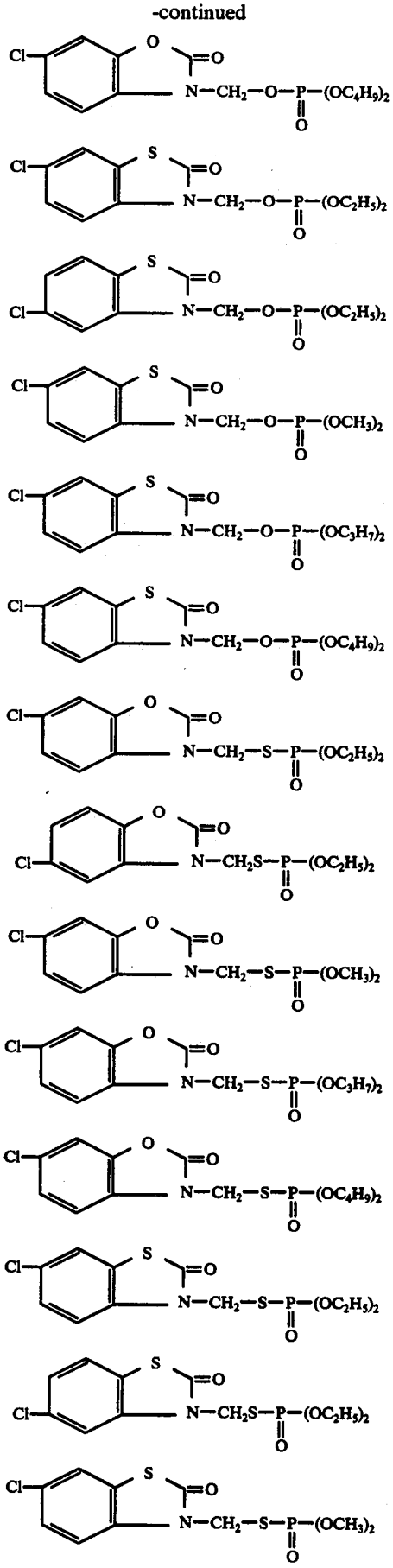
-continued
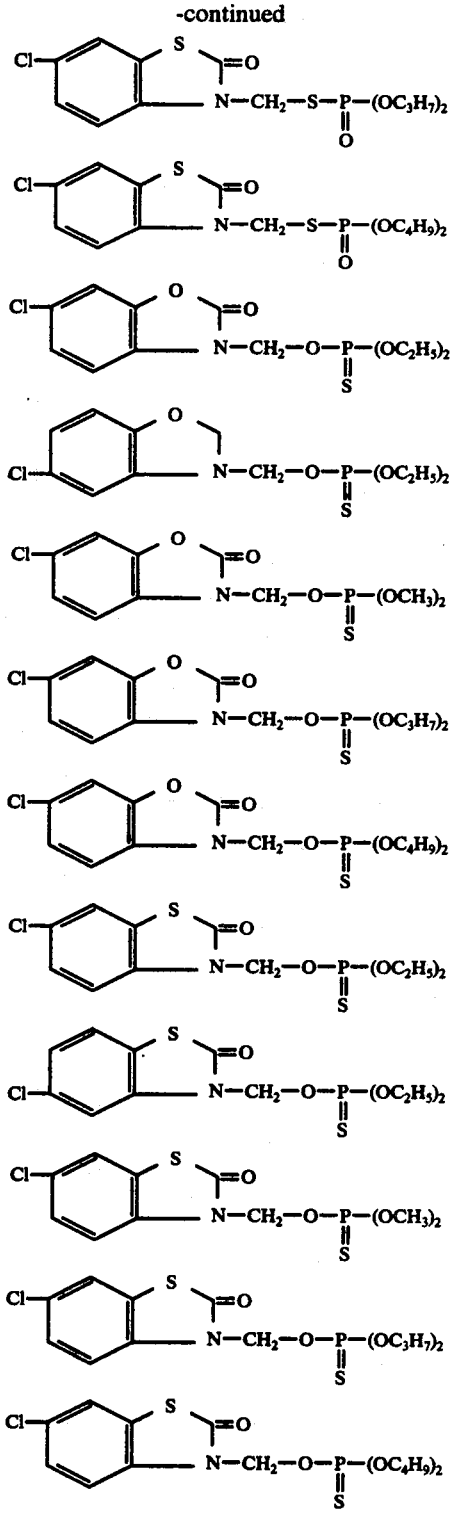
The O,O-dialkyl-(1,2-dicarbalkoxy alkyl) diphosphates have the structure:
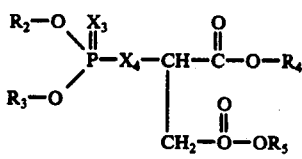
II wherein $X_3$ and $X_4$ are oxygen or sulfur, and can be the same or different; and $R_2$, $R_3$, $R_4$ and $R_5$ are alkyl groups having from one to about four carbon atoms, and can be the same or different.

Preferably, $X_3$ and $X_4$ are sulfur, $R_2$ and $R_3$ are methyl, and $R_4$ and $R_5$ are ethyl, in which case the compound is malathion.

Other compounds in this class include:

$$(CH_3-O)_2P(=S)-S-CH(-C(=O)-O-C_2H_5)-CH_2-C(=O)-O-CH_3$$

$$(C_2H_5-O)(CH_3-O)P(=S)-S-CH(-C(=O)-O-CH_3)-CH_2-C(=O)-O-CH_3$$

$$(C_3H_7-O)_2P(=S)-S-CH(-C(=O)-O-C_2H_5)-CH_2-C(=O)-O-C_2H_5$$

$$(C_4H_9-O)_2P(=S)-S-CH(-C(=O)-O-C_4H_9)-CH_2-C(=O)-O-C_4H_9$$

$$(CH_3-O)_2P(=S)-S-CH(-C(=O)-O-CH_3)-CH_2-C(=O)-O-CH_3$$

$$(CH_3-O)_2P(=S)-O-CH(-C(=O)-O-C_2H_5)-CH_2-C(=O)-O-CH_2$$

$$(C_2H_5-O)(CH_3-O)P(=O)-O-CH(-C(=O)-O-CH_3)-CH_2-C(=O)-O-CH_3$$

$$(C_3H_7-O)_2P(=O)-O-CH(-C(=O)-O-C_2H_5)-CH_2-C(=O)-O-C_2H_5$$

$$(C_4H_9-O)_2P(=O)-O-CH(-C(=O)-O-C_4H_9)-CH_2-C(=O)-O-C_4H_9$$

-continued $$(CH_3-O)_2P(=O)-O-CH(-C(=O)-O-CH_3)-CH_2-C(=O)-O-CH_3$$

$$(CH_3-O)_2P(=S)-O-CH(-C(=O)-O-C_2H_5)-CH_2-C(=O)-O-CH_3$$

$$(C_2H_5-O)(CH_3-O)P(=S)-O-CH(-C(=O)-O-CH_3)-CH_2-C(=O)-O-CH_3$$

$$(C_3H_7-O)_2P(=S)-O-CH(-C(=O)-O-C_2H_5)-CH_2-C(=O)-O-C_2H_5$$

$$(C_4H_9-O)_2P(=S)-O-CH(-C(=O)-O-C_4H_9)-CH_2-C(=O)-O-C_4H_9$$

$$(CH_3-O)_2P(=S)-O-CH(-C(=O)-O-CH_3)-CH_2-C(=O)-O-CH_3$$

$$(CH_3-O)_2P(=O)-S-CH(-C(=O)-O-C_2H_5)-CH_2-C(=O)-O-CH_3$$

$$(C_2H_5-O)(CH_3-O)P(=O)-S-CH(-C(=O)-O-CH_3)-CH_2-C(=O)-O-CH_3$$

$$(C_3H_7-O)_2P(=O)-S-CH(-C(=O)-O-C_2H_5)-CH_2-C(=O)-O-C_2H_5$$

$$(C_4H_9-O)_2P(=O)-S-CH(-C(=O)-O-C_4H_9)-CH_2-C(=O)-O-C_4H_9$$

-continued

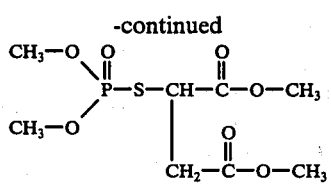

The proportions of each phosphate ester can be widely varied, but in general a synergistically enhanced arthropodicidal, i.e., insecticidal and miticidal, effect is obtained at ratios of O,O-dialkyl-diphosphoryl methylhalo-6-benzothiazolone to O,O-dialkyl-(1,2-dicarbalkoxyalkyl) diphosphate within the range from 0.225:1 to 50:1; and preferably from 10:1 to 20:1.

The compositions of the invention show excellent pesticidal activity against all orders of harmful insects, and suborders of harmful mites and ticks.

Exemplary insects are Thysanura such as the silverfish *Lepisma saccharina;* Orthoptera such as the German cockroach *Blattela germanica;* Isoptera such as the termite *Reticulitermes santoninsis;* Dermaptera such as the earwig *Forficula auricularia;* Anoplura such as the hog louse *Haematopinus suis;* Mallophaga such as the chicken body louse *Menacanthus stramineus;* Thysanoptera such as the citrus thrip *Scirtothrips citri:* Hemiptera such as the tarnished plant bug *Lygus lineolaris;* Homoptera such as the rosy apple aphid *Dysaphis plantaginea* and the pear psylla *Psylla pyricola;* Coleoptera such as the plum curculio *Conotrachelus nenuphar* and the striped cucumber beetle *Acalymma vittata;* Lepidoptera such as the southern armyworm *Spodoptera eridania* and the codling moth *Laspeyresia pomonella;* Diptera such as the apple maggot *Rhagoletis pomonella* and the cherry fruit fly *Rhagoletis cingulata;* Siphonaptera such as the dog flea *Ctenocephalides canis;* Hymenoptera such as the rose sawfly *Caliroa aethiops* and springtails (Collembola).

The compositions according to the present invention are especially effective when combating representatives of the order Acarina. Exemplary suborders of mites and ticks are Mesostigmata such as the chicken mite, *Dermanyssus gallinae;* Ixodides such as the American dog tick, *Dermacentor variabilis;* Sarcoptiformes such as the itch mite *Sarcoptes scabiei;* Trombidiformes such as the maple bladdergall mite *Vasates quadripedes,* the twospotted spider mite *Tetranychus urticae,* and the European red mite *Panonychus ulmi.*

The compositions of the invention are also effective against members of the class Diplopoda (millipedes) and the orders Isopoda (sowbugs) and Araneida (spiders).

These compositions can include the two insecticides-acaracides and also if desired inert carriers and/or other additives known to be useful in insecticidal-acaricidal compositions.

These compositions can include the two arthropodicides and also if desired inert carriers and/or other additives known to be useful in insecticidal acaricidal compositions. The inert carriers and additives can be solid or liquid, and include mineral salts, solvents, diluents, dispersing agents, emulsifiers, wetting agents, adhesives, thickeners, binders and fertilizers. Biocidal compounds can also be added, such as the ureas, the saturated or unsaturated halogen-fatty acids, halogenobenzonitriles, halogenobenzoic acids, phenoxyalkylcarboxylic acids, triazines, nitroalkylphenols, organic phosphoric acid compounds, quaternary ammonium salts, sulphamic acids, arsenates, arsenites, borates or chlorates.

The compositions can be in the form of solutions, emulsions, suspensions, granules or dusting agents. The forms of application depend on the end uses and ensure that the active substances are finely distributed.

The content of active arthropodicides according to the invention is within the range from 0.1 and 95%. For application from aircraft or other suitable forms, concentrations of up to 99.5% or even pure active substance combinations can be employed.

Solutions are prepared using solvents for the arthropodicides such as aliphatic alcohols, for example ethyl alcohol or isopropyl alcohol, aliphatic ketones, such as acetone or cyclohexanone, aliphatic hydrocarbons, such as kerosene, and cyclic hydrocarbons, such as benzene, toluene, xylene, tetrahydronaphthalene, alkylated naphthalenes, chlorinated hydrocarbons, such as tetrachlorethane and ethylene chloride, and mineral and vegetable oils or mixtures of the above mentioned substances.

Aqueous preparations in the form of emulsions and dispersions are especially useful. The active arthropodicides according to the invention, suitably in solution in a solvent, are homogenized in water, preferably by means of wetting agents or dispersing agents; quaternary ammonium compounds may be mentioned as examples of cationic emulsifiers or dispersing agents; soaps, aliphatic long-chain sulphuric acid monoesters, aliphatic-aromatic sulphonic acids and lone-chain alkoxyacetic acids may be mentioned as examples of anionic agents; any polyglycol ethers of fatty alcohols or ethylene oxide condensation products with p-tertalkylphenols may be mentioned amongst non-ionic agents.

It is also possible to formulate concentrates of the active substance, emulsifier or dispersing agent, and optionally solvents. Such concentrates can be diluted before use, for example, with water.

Dusting agents can be made by mixing or grinding the active arthropodicides according to the invention with a solid carrier. Solid carriers are, for example: talc, diatomaceous earth, kaolin, bentonite, calcium carbonate, boric acid and tricalcium phosphate, wood flour, cork powder, charcoal and other materials of vegetable origin. Alternatively, the substances can be absorbed on the carriers, using a volatile solvent. Pulverulent preparations and pastes can be made capable of suspension in water, and used as spraying agents, by adding wetting agents and protective colloids.

In many cases the use of granules for gradual release of the active substance combination over a prolonged period of time is of advantage. These can be manufactured by dissolving the active substances in an organic solvent, absorbing this solution by a granular material, for example attapulgite or $SiO_2$, and removing the solvent. They can also be manufactured by mixing the active substance combination with polymerisable compounds, after which polymerisation is carried out which leaves the active substances unaffected, the granulation being carried out whilst the polymerisation is still proceeding.

The following Examples in the opinion of the inventors represent preferred embodiments of the invention.

EXAMPLE 1

The toxicity response from *Tetranychus urticae* Koch treated with (1) Zolone 34.9% EC (phosalone), (2) Malathion 95% Tech, and (3) combinations of Zolone EC and Malathion Tech, was studied in the following experiments:

Mites used in this study were obtained from a University of Kentucky greenhouse culture maintained free from phosphate ester acaricide contact (phosphate-susceptible strain), and a New Jersey culture maintained in contact with phosphate ester acaricide (phosphate-resistant strain).

Thirty 8 day old T. urticae female mites were dipped into the solutions noted in Table I below. Mortality data were taken 48 hours after treatment. The test was repeated providing about 300 mites per treatment.

A 10,000 PPM stock solution of Malathion in acetone was used, and all formulations were mixed with tap water containing 1 drop of Triton X-207 per 500 ml of water.

The synergism of Zolone and Maathion as compared with either alone is shown in Tables I and II aganist both phosphate-susceptible and phosphate-resistant mites:

TABLE I

Mortality of T. urticae (Ky.[b] strain) at various concentrations of Zolone and Malathion and the synergistic activity of Zolone-Malathion mixture.

| Example No. | Arthropodicide | Conc. lbs ai/100 gal | %mortality[a] |
|---|---|---|---|
| Control A | Zolone EC (phosalone) | 0.188 (0.5 pt) | 23.9 |
| | | 0.375 (1.0 pt) | 47.1 |
| | | 0.750 (1.0 qt) | 60.6 |
| Control B | Malathion | 0.00835 (10 PPM) | 1.6 |
| | | 0.0835 (100 PPM) | 5.1 |
| | | 0.835 (1000 PPM) | 62.7 |
| Example 1 | Zolone EC + Malathion | 0.188:0.00835 | 65.4 |
| | | 0.188:0.0835 | 79.5 |
| | | 0.188:0.835 | 100.0 |
| | | 0.375:0.00835 | 98.3 |
| | | 0.375:0.0835 | 99.6 |
| | | 0.375:0.835 | 100.0 |

[a] Control corrected mortality by Abbot's Formula
[b] A phosphate-susceptible strain of predacious mites commonly found in apple orchards.

TABLE II

Mortality of T. urticae NJ[b] strain) at various concentrations of Zolone, Malathion, and Zolone-Malathion mixture.

| Example No. | Test material | Conc. lbs. ai/100 gal. | %mortality[a] |
|---|---|---|---|
| Control A | Zolone EC (phosalone) | 0.188 (0.5 pt | 18.9 |
| | | 0.375 (1.0 pt) | 32.5 |
| | | 0.750 (1.0 qt) | 63.6 |
| Control B | Malathion | 0.00835 (10 PPM) | 0 |
| | | 0.0835 (100 PPM) | 2.1 |
| | | 0.835 (1000 PPM) | 25.4 |
| Example 1 | Zolone EC + Malathion | 0.188:0.00835 | 32.2 |
| | | 0.188:0.0835 | 77.9 |
| | | 0.188:0.835 | 100 |
| | | 0.375:0.00835 | 64.2 |
| | | 0.375:0.0835 | 84.3 |
| | | 0.375:0.835 | 100 |

[a] Control corrected mortality by Abbot's formula
[b] A phosphate-resistant strain of predacious mites commonly found in apple orchards.

It is apparent from the above data that the mixture of malathion and phosalone in accordance with the invention is synergistically more effective than either alone against both phosphate-susceptible and phosphate-resistant mites. The degree of enhancement of miticidal activity is in fact remarkable, since it is several times that of either alone, in the same concentration, and is clearly far more than merely additive.

EXAMPLE 2

In these experiments, the relative toxicity of Zolone EC, malathion, and Zolone EC plus malathion is measured by induced 72-hour mortality of southern armyworm larvea.

Zolone EC was diluted to desired concentrations in deionized water. Malathion (95%) was dissolved in 10% acetone emulsion base, and then diluted to desired concentrations in deionized water.

Individually potted horticultural bean (Phaeseolus vulgaris), Dwarf French cultivar, plants in first true leaf growth stage, were used as host plants. Upper and lower surfaces of foliar portions were alternately sprayed at 20 psi to incipient run-off, allowed to air dry under laboratory conditions, and then removed to greenhouse holding racks provided with subterranean water source. Five third-instar larvae were caged on each plant for 72 hours. Ten test plants (replicates) were used for each test unit.

At the end of the 72-hour holding period, observations were made for insect mortality, any abnormal physiological responses and plant injury. Phytotoxicity is rated on a zero (no injury) to ten (death of the test plant) scale.

The toxicity data obtained appear in Table III below:

TABLE III

Toxicity of Zolone EC, Malathion and Zolone EC plus Malathion as measured by induced 72-hour mortality of Southern Armyworm larvae.

Spodoptera eridania, 3rd instar

| Example No. | Treatment applied | Test Concentration Lbs a.i./100 gal | Ave % Mortality 72 hours |
|---|---|---|---|
| Control A | Zolone EC | 0.188 | 40 |
| | | 0.375 | 64 |
| | | 0.750 | 90 |
| Control B | Malathion | 0.00835 | 4 |
| | | 0.0835 | 34 |
| | | 0.835 | 90 |
| Example 2 | Zolone EC + Malathion | 0.188 + 0.00835 | 92 |
| | | 0.188 + 0.0835 | 96 |
| | | 0.188 + 0.835 | 100 |
| | | 0.375 + 0.00835 | 94 |
| | | 0.375 + 0.835 | 88 |
| | | 0.375 + 0.835 | 100[2] |
| | | 0.375 + 0.08 | 80 |
| | Untreated controls | | 4 |

[2] 100% mortality all replicates in 24 hours

The data in Table III indicate quite clearly that Zolone EC in combination with malathion is more toxic to southern armyworm larvae as a stomach poison than either Zolone EC or malathion alone.

It is significant to note that Zolone EC plus malathion (0.375 + 0.835 lbs a.i./100 gal) induced 100% mortality in 24 hours. Zolone EC plus malathion (0.188 + 0.835 lbs a.i./100 gal) induced 100% control but was slower acting, requiring 72 hours to induce complete control.

The reason for the potentiation of malathion by phosalone and of phosalone by malathion is not understood, and has not been established. It is however suggested that one of the possible reasons for malathion resistance is some insects and mites is a high carboxylesterase level, which detoxifies malathion before it can kill them. Phosalone inhibits carboxylesterase, and it is therefore possible that the phosalone blocks carboxylesterase, and thereby makes it possible to kill certain arthropods with malathion that were previously malathion-resistant. The result is a mixture which is capable of killing phosphate-resistant arthropods, i.e., insects and mites.

EXAMPLE 3

The toxicity response from *Tetranychus urticae Koch* treated with (1) Parathion -O,O-diethyl-O-p-nitrophenyl phosphorothioate (2) Phosdrin - dimethyl phosphate of methyl-3-hydroxy-cis-crotonate and (3) combinations of Parathion and Phosdrin is studied.

Thirty 8 day old *T. urticae* female mites are dipped into solutions of the above arthropodicides as noted in Table IV below. Mortality data are taken 48 hours after treatment. The tests provide about 300 mites per treatment.

All formulations are mixed with tap water containing 1 drop of Triton X-207 per 500 ml of water.

TABLE IV

| Example No. | Arthropodicide | Conc. lbs ai/100 gal |
|---|---|---|
| Control C | Parathion | 0.188 (0.5 pt) |
| | | 0.375 (1.0 pt) |
| | | 0.750 (1.0 qt) |
| Control D | Phosdrin | 0.00835 (10 PPM) |
| | | 0.0835 (100 PPM) |
| | | 0.835 (1000 PPM) |
| Example 3 | Parathion + Phosdrin | 0.188:0.00835 |
| | | 0.188:0.0835 |
| | | 0.188:0.835 |
| | | 0.375:0.00835 |
| | | 0.375:0.0835 |
| | | 0.375:0.835 |

The mixture of parathion and phosdrin in accordance with the invention is synergistically more effective than either alone against both phosphate-susceptible and phosphate-resistant mites.

EXAMPLE 4

The toxicity response from *Tetranychus urticae Koch* treated with (1) Ethion - (2-chloroethyl) phosphonic acid, (2) Malathion 95% Tech, and (3) combinations of Ethion and Malathion Tech, is studied.

Thirty 8 day old *T. urticae* female mites are dipped into the solutions noted in Table V below. Mortality data are taken 48 hours after treatment. The tests provide about 300 mites per treatment.

All formulations are mixed with tap water containing 1 drop of Triton X-207 per 500 ml of water.

TABLE V

| Example No. | Arthropodicide | Conc. lbs ai/100 gal |
|---|---|---|
| Control E | Ethion | 0.188 (0.5 pt) |
| | | 0.375 (1.0 pt) |
| | | 0.750 (1.0 qt) |
| Control F | Malathion | 0.00835 (10 PPM) |
| | | 0.0835 (100 PPM) |
| | | 0.835 (1000 PPM) |
| Example 4 | Ethion + Malathion | 0.188:0.00835 |
| | | 0.188:0.0835 |
| | | 0.188:0.835 |
| | | 0.375:0.00835 |
| | | 0.375:0.0835 |
| | | 0.375:0.835 |

The mixture of Ethion and Malathion in accordance with the invention is synergistically more effective than either alone against both phosphate-susceptible and phosphate-resistant mites.

EXAMPLE 5

The toxicity response from *Tetranychus urticae Koch* treated with (1) Trithion-S-((p-chlorophenylthio)methyl) O,O-diethyl phosphorodithioate, (2) Phenthoate-O,O-dimethyl-S-(α-ethoxycarbonylbenzyl)-phosphorodithioate and (3) combinations of Trithion and Phenthoate is studied.

Thirty 8 day old *T. urticae* female mites are dipped into the solutions noted in Table VI below. Mortality data are taken 48 hours after treatment. The tests provide about 300 mites per treatment.

All formulations are mixed with tap water containing 1 drop of Triton X-207 per 500 ml of water.

TABLE VI

| Example No. | Arthropodicide | Conc. lbs ai/100 gal |
|---|---|---|
| Control G | Trithion | 0.188 (0.5 pt) |
| | | 0.375 (1.0 pt) |
| | | 0.750 (1.0 qt) |
| Control H | Phenthoate | 0.00835 (10 PPM) |
| | | 0.0835 (100 PPM) |
| | | 0.835 (1000 PPM) |
| Example 5 | Trithion + Phenthoate | 0.188:0.00835 |
| | | 0.188:0.0835 |
| | | 0.188:0.835 |
| | | 0.375:0.00835 |
| | | 0.375:0.0835 |
| | | 0.375:0.835 |

The mixture of trithion and phenthoate in accordance with the invention is synergistically more effective than either alone against both phosphate-susceptible and phosphate-resistant mites.

EXAMPLE 6

The toxicity response from *Tetranychus urticae Koch* treated with (1) Guthion-O,O-Diethyl-S-(4-oxo-1,2,3-benzotriazin-3 (4H)-ylmethyl)-phosphorodithioate, (2) Malathion 95% Tech, and (3) combinations of Guthion and Malathion Tech, is studied.

Thirty 8 day old *T. urticae* female mites are dipped into the solutions noted in Table VII below. Mortality data are taken 48 hours after treatment. The tests provide about 300 mites per treatment.

All formulations are mixed with tap water containing 1 drop of Triton X-207 per 500 ml of water.

TABLE VII

| Example No. | Arthropodicide | Conc. lbs ai/100 gal |
|---|---|---|
| Control I | Guthion | 0.188 (0.5 pt) |
| | | 0.375 (1.0 pt) |
| | | 0.750 (1.0 qt) |
| Control J | Malathion | 0.00835 (10 PPM) |
| | | 0.0835 (100 PPM) |
| | | 0.835 (1000 PPM) |
| Example 6 | Guthion + Malathion | 0.188:0.00835 |
| | | 0.188:0.0835 |
| | | 0.188:0.835 |
| | | 0.375:0.00835 |
| | | 0.375:0.0835 |
| | | 0.375:0.835 |

The mixture of Guthion and Malathion in accordance with the invention is synergistically more effective than either alone against both phosphate-susceptible and phosphate-resistant mites.

EXAMPLE 7

The toxicity response from *Tetranychus urticae Koch* treated with (1) DDVP -2,2-dichlorovinyl dimethyl phosphate (2) Phosdrin - dimethyl phosphate of methyl-3-hydroxy-cis-crotonate and (3) combinations of DDVP and Phosdrin is studied.

Thirty 8 day old *T. urticae* female mites are dipped into the solutions noted in Table VIII below. Mortality data are taken 48 hours after treatment. The tests provide about 300 mites per treatment.

All formations are mixed with tap water containing 1 drop of Triton X-207 per 500 ml of water.

TABLE VIII

| Example No. | Arthropodicide | Conc. lbs ai/100 gal |
|---|---|---|
| Control K | DDVP | 0.188 (0.5 pt) |
| | | 0.375 (1.0 pt) |
| | | 0.750 (1.0 qt) |
| Control L | Phosdrin | 0.00835 (10 PPM) |
| | | 0.0835 (100 PPM) |
| | | 0.835 (1000 PPM) |
| Example 7 | DDVP + Phosdrin | 0.188:0.00835 |
| | | 0.188:0.0835 |
| | | 0.188:0.835 |
| | | 0.375:0.00835 |
| | | 0.375:0.0835 |
| | | 0.375:0.835 |

The mixture of DDVP and Phosdrin in accordance with the invention is synergistically more effective than either alone against both phosphate-susceptible and phosphate-resistant mites.

EXAMPLE 8

The toxicity response from *Tetranychus urticae Koch* treated with (1) Dimethoate-O,O-dimethyl S-(N-methylcarbamoyl-methyl) phosphorodithioate, (2) Phenthoate-O,O-dimethyl S-(α-ethoxycarbonylbenzyl)-phosphorodithioate, and (3) combinations of Dimethoate and Phenthoate is studied.

Thirty 8 day old *T. urticae* female mites are dipped into the solutions noted in Table IX below. Mortality data are taken 48 hours after treatment. The tests provide about 300 mites per treatment.

All formulations are mixed with tap water containing 1 drop of Triton X-207 per 500 ml of water.

TABLE IX

| Example No. | Arthropodicide | Conc. lbs ai/100 gal |
|---|---|---|
| Control M | Dimethoate | 0.188 (0.5 pt) |
| | | 0.375 (1.0 pt) |
| | | 0.750 (1.0 qt) |
| Control N | Phenthoate | 0.00835 (10 PPM) |
| | | 0.0835 (100 PPM) |
| | | 0.835 (1000 PPM) |
| Example 8 | Dimethoate + Phenthoate | 0.188:0.00835 |
| | | 0.188:0.0835 |
| | | 0.188:0.835 |
| | | 0.375:0.00835 |

TABLE IX-continued

| Example No. | Arthropodicide | Conc. lbs ai/100 gal |
|---|---|---|
| | | 0.375:0.0835 |
| | | 0.375:0.835 |

The mixture of dimethoate and phenthoate in accordance with the invention is synergistically more effective than either alone against both phosphate-susceptible and phosphate-resistant mites.

Having regard to the foregoing disclosure, the following is claimed as inventive, and patentable embodiments thereof:

1. An arthropodicidal composition having an enhanced effectiveness against phosphate-resistant arthropods comprising O,O-diethyl-dithiophosphorylmethyl-3-chloro-6-benzoxazolone and O,O-dimethyl-S-(1,2-dicarbethoxyethyl), dithiophosphate, the weight ratio of amounts of O,O-diethyl-dithiophosphoryl-methyl-3-chloro-6-benzoxazolone and O,O-dimethyl-S-(1,2-dicarbethoxy ethyl) dithiophosphate being within the range from about 0.225:1 to about 50:1, the amounts of O,O-diethyl-dithiophosphoryl-methyl-3-chloro-6-benzoxazolone and O,O-dimethyl-S-(1,2-dicarbethoxy ethyl) dithiophosphate being selected within the stated range, each to synergize the effectiveness of the other.

2. A composition according to claim 1, in which the ratio is within the range from 10:1 to 20:1.

3. A composition according to claim 1, comprising an inert carrier and a content of active arthropodicide within the range from about 0.1 to about 95%.

4. A composition according to claim 3, in the form of a solution of active anthropodicides in a solvent therefor as the inert carrier.

5. A composition according to claim 4, in the form of an aqueous emulsion of the solution of the active arthropodicides in a solvent and comprising a wetting agent or dispersing agent.

6. A composition according to claim 4, in which the carrier is a solid and the composition is in particulate form.

7. A process for control of arthropods, which comprises applying to the arthropod a toxic amount of a composition according to claim 1.

* * * * *

UNITED STATES PATENT OFFICE
CERTIFICATE OF CORRECTION

Patent No. 4,064,237    Dated December 20, 1977

Inventor(s) Michael A. Gallo et al

It is certified that error appears in the above-identified patent and that said Letters Patent are hereby corrected as shown below:

Column 5, line 20 :

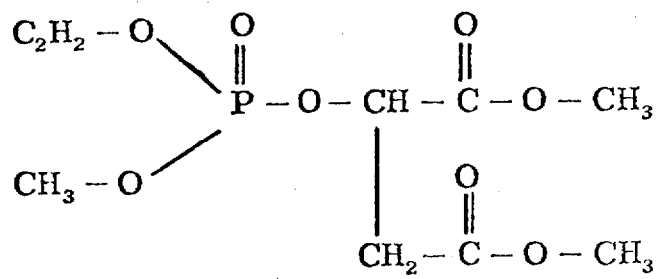

should be

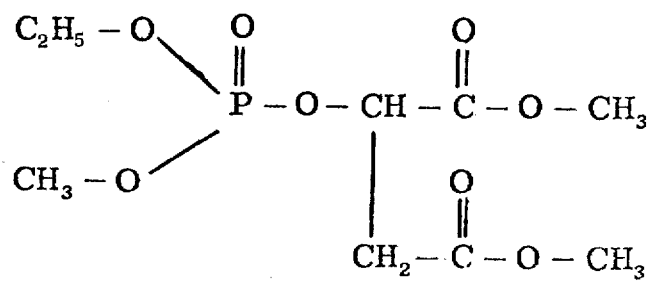

UNITED STATES PATENT OFFICE
CERTIFICATE OF CORRECTION

Patent No. 4,064,237  Dated December 20, 1977

Inventor(s) Michael A. Gallo et al

It is certified that error appears in the above-identified patent and that said Letters Patent are hereby corrected as shown below:

Column 5, line 45 :

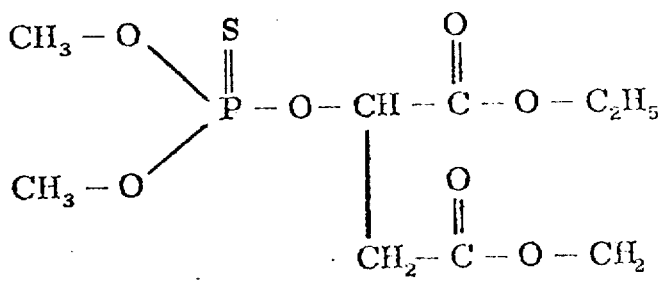

should be

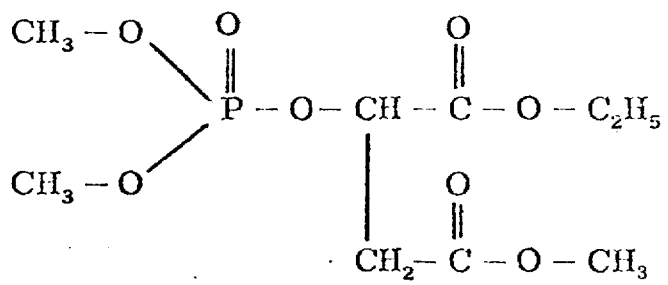

UNITED STATES PATENT OFFICE
CERTIFICATE OF CORRECTION

Patent No. 4,064,237      Dated December 20, 1977

Inventor(s) Michael A. Gallo et al

It is certified that error appears in the above-identified patent and that said Letters Patent are hereby corrected as shown below:

Column 5, line 50 :

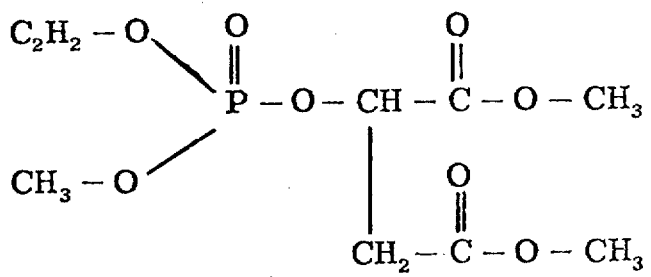

should be

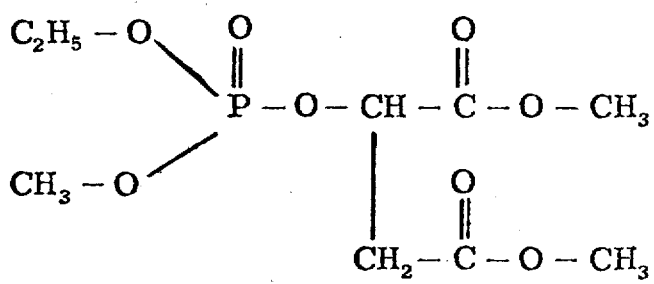

UNITED STATES PATENT OFFICE
CERTIFICATE OF CORRECTION

Patent No. 4,064,237　　　　　　　　　　Dated December 20, 1977

Inventor(s) Michael A. Gallo et al

It is certified that error appears in the above-identified patent and that said Letters Patent are hereby corrected as shown below:

Column 6, line 15 :

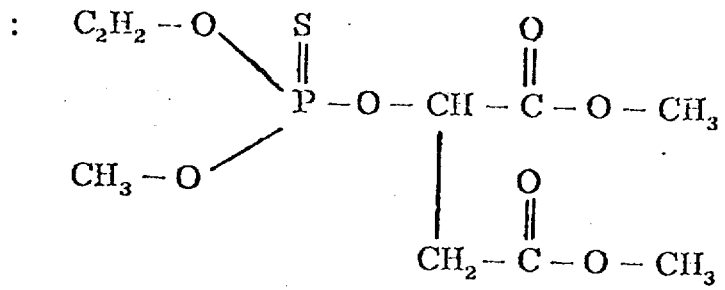

should be

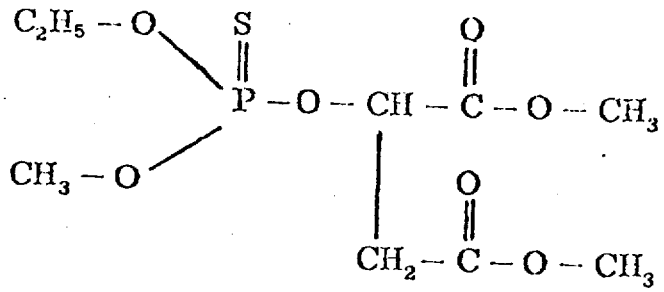

UNITED STATES PATENT OFFICE
CERTIFICATE OF CORRECTION

Patent No. 4,064,237　　　　　Dated December 20, 1977

Inventor(s) Michael A. Gallo et al

It is certified that error appears in the above-identified patent and that said Letters Patent are hereby corrected as shown below:

Column 6, line 50 :

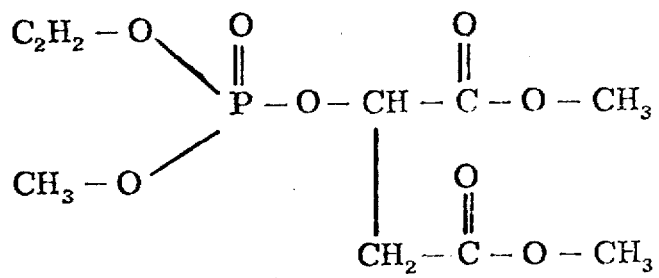

should be

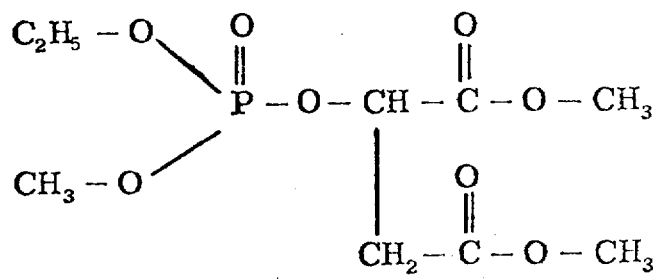

UNITED STATES PATENT OFFICE
CERTIFICATE OF CORRECTION

Patent No. 4,064,237            Dated December 20, 1977

Inventor(s) Michael A. Gallo et al

It is certified that error appears in the above-identified patent and that said Letters Patent are hereby corrected as shown below:

| | | |
|---|---|---|
| Column 8, line 67 | : | "34.9%" should be --34.8%-- |
| Column 9, line 17 | : | "maathion" should be --malathion-- |
| Column 9, line 18 | : | "aganist" should be --against-- |
| Column 10, line 40 Table III, Col 3 | : | "0.375 + 0.835" should be --0.375 + 0.0835-- |

Signed and Sealed this

Twenty-seventh Day of June 1978

[SEAL]

Attest:

RUTH C. MASON
*Attesting Officer*

DONALD W. BANNER
*Commissioner of Patents and Trademarks*